United States Patent [19]

DeFelice

[11] Patent Number: 5,560,928
[45] Date of Patent: Oct. 1, 1996

[54] NUTRITIONAL AND/OR DIETARY COMPOSITION AND METHOD OF USING THE SAME

[76] Inventor: Stephen L. DeFelice, 235 Munsee Way, Westfield, N.J. 07090

[21] Appl. No.: 494,100

[22] Filed: Jun. 23, 1995

[51] Int. Cl.$^6$ .............................. A61K 9/16; A61K 9/22
[52] U.S. Cl. .................... 424/466; 424/468; 424/469; 424/470; 424/489; 424/490; 424/495; 514/781
[58] Field of Search .................. 424/466, 468, 424/469, 470, 458, 461, 489, 490, 495

[56] References Cited

U.S. PATENT DOCUMENTS

| | | | |
|---|---|---|---|
| 3,773,920 | 11/1973 | Nakamoto et al. | 424/19 |
| 4,122,157 | 10/1978 | Huber | 424/21 |
| 4,503,031 | 3/1985 | Glassman | 424/15 |
| 4,684,516 | 8/1987 | Bhutani | 424/19 |
| 4,725,427 | 2/1988 | Ashmead et al. | 424/44 |
| 4,752,479 | 6/1988 | Briggs et al. | 424/472 |
| 5,055,306 | 10/1991 | Barry et al. | 424/482 |
| 5,178,878 | 1/1993 | Wehling et al. | 424/466 |
| 5,200,193 | 4/1993 | Radebaugh et al. | 424/468 |
| 5,211,957 | 5/1993 | Hagemann et al. | 424/466 |
| 5,223,264 | 6/1993 | Wehling et al. | 424/466 |
| 5,306,506 | 4/1994 | Zema et al. | 424/466 |
| 5,376,384 | 12/1994 | Eichel et al. | 424/480 |

*Primary Examiner*—James M. Spear
*Attorney, Agent, or Firm*—Watov & Kipnes, P.C.

[57] ABSTRACT

A composition and method of using the same which provides in as little as a single dose covering a 24 hour period a nutritional and/or dietary supplement which provides administration of water soluble and water insoluble active ingredients for immediate and sustained-release delivery.

28 Claims, No Drawings

NUTRITIONAL AND/OR DIETARY COMPOSITION AND METHOD OF USING THE SAME

FIELD OF THE INVENTION

The present invention is directed to a nutritional/dietary composition capable of providing at least one nutritional and/or dietary supplement including free form and sustained-release compounds in solid or liquid dosage form.

BACKGROUND OF THE INVENTION

It has become increasingly important for the prevention and treatment of disease as well as the maintenance of good health for people to supplement the normal intake of food with nutritional and/or dietary supplements. Typically, these substances are required to be taken several times a day in order to fulfill the daily dosage requirements. Many nutritional and/or dietary substances are not well stored by the body requiring frequent dosing. However, the more doses required, the less compliance there is by the patient. People simply will not take the number of pills required to complete the daily dosage requirements. The reasons for failing to take proper dosages include inconvenience, difficulty in swallowing pills, forgetfulness and the like. In addition, the generally poor taste of many nutritional and/or dietary substances adds to the difficulty in completing dosage regimens.

There have been efforts to develop dosage systems which seek to make active ingredients more pleasant and effective for the consumer. In order to provide a pleasant tasting composition and one which provides the desired benefits, it is necessary for the nutritional and/or dietary dosage system meet the following requirements.

The system must provide for both nutritional and dietary active ingredients. The system must also be able to deliver both water soluble and water insoluble active ingredients. A sustained-release system must also be provided so that active ingredients which are required to be administered over a long period may be slowly delivered rather than all at once. The formulation must be readily dissolvable in a liquid, particularly water to provide a pleasant tasting drink. Finally, administration of the composition must be sufficient to provide an optimum delivery of the active ingredients so that the composition is effective until the next dosage which may be as much as approximately 24 hours later.

Efforts have been made to meet the above-stated criteria of a nutritional and/or dietary supplement formulation. For example, Nakomoto, U.S. Pat. No. 3,773,920, discloses sustained-release granules which provide for a water soluble medicament contained within an ethylcellulose polymer to provide uniform release velocity and complete release of the medicament.

Huber, U.S. Pat. No. 4,122,157, discloses a preparation for the administration of nitrofurantoin. The composition is in the form of a sustained-release tablet which is taken orally. The tablet contains a rapid release component and a slow release component for the same drug. It is further stated that the composition contains an effervescent agent.

Glassman, U.S. Pat. No. 4,503,031, discloses a two section tablet for the administration of drugs including a sustained-release component. Sodium bicarbonate is employed as an effervescent agent.

Ashmead, U.S. Pat. No. 4,725,427, discloses a vitamin-mineral combination for both water soluble and water insoluble active ingredients. An effervescent agent is provided so that the composition is dissolvable in water.

Briggs et al., U.S. Pat. No. 4,752,479, disclose an iron containing dietary supplement for oral administration in which an inner core contains iron and a waxy film former of ethylcellulose is provided around the core.

Barry et al., U.S. Pat. No. 5,055,306, disclose an effervescent tablet which includes a sustained-release formulation comprising a core containing the active ingredient and a coating which is water swellable.

Wehling et al., U.S. Pat. No. 5,178,878, disclose an effervescent composition for oral administration which employs microparticles of an active ingredient including vitamins and minerals.

Radebaugh et al., U.S. Pat. No. 5,200,193, disclose tablets which contain a sustained-release formulation using ethylcellulose as a matrix. The tablets contain drugs such as ibuprofen as the active ingredient.

Hagemann et al., U.S. Pat. No. 5,211,957, disclose an effervescent tablet for diclofenac providing both immediate and delayed release of the active ingredient.

Wehling et al., U.S. Pat. No. 5,223,264, disclose an oral pediatric vitamin supplement in tablet form containing an effervescent agent.

Zema et al., U.S. Pat. No. 5,306,506, disclose a water composition containing a drug as an active ingredient which is microencapsulated to delay release and mask the taste of the active ingredient. Ethylcellulose is used as a membrane for the microencapsulation.

Eichel et al., U.S. Pat. No. 5,376,384, disclose a sustained-release formulation for water soluble drugs employing a diffusion barrier.

While all of these references disclose dosage formulations effectively administering an active ingredient through tablet or liquid form, none of the references provide an acceptable means of administering a nutritional and/or dietary supplement in as little as a single daily dosage form which can accommodate both water soluble and water insoluble nutritional and/or dietary active ingredients and provide a system by which the same can be delivered both immediately and through sustained-release.

SUMMARY OF THE INVENTION

The present invention is generally directed to a pharmaceutical composition for providing a dosage formulation for the administration of nutritional and/or dietary supplements as few as once in a 24 hour period.

In particular, the present invention is directed to a nutritional/dietary composition comprising:

(a) at least one active ingredient selected from the group consisting of a nutritional supplement, a dietary supplement and combinations thereof in an amount sufficient to provide a dosage form of said active ingredients as few as once in a 24 hour period, said active ingredients being in the form of both a free form component and a microencapsulated component which is in a sustained release form; and (b) an effective amount of an effervescent agent.

DETAILED DESCRIPTION OF THE INVENTION

The present invention is directed to a composition uniquely suited for patients requiring a nutritional and/or dietary supplement. The present invention provides a formulation which delivers a sufficient amount of the active ingredients including water soluble compounds, water insoluble compounds and combinations and variations thereof to provide a dosage form so that the patient need take the supplement as little as only once during a 24 hour period. The patient therefore need not be concerned with taking several pills during the day with the possibility of missing a dose and thereby reducing the effectiveness of the therapy. The present invention is particularly suited to those who have difficulty in swallowing the pills and/or the elderly because the present formulation can be provided in liquid form.

The active ingredients which may be employed in the present invention include nutritional supplements, dietary supplements and combinations thereof. The compounds meeting this criteria may have varying degrees of solubility in water ranging from highly soluble to insoluble. These compounds generally include vitamins, minerals, amino acids, herbal and botanical products and the like. Vitamins generally refer to organic substances that are required in the diet and include thiamin, riboflavin, nicotinic acid, pantothenic acid, pyrodoxine, biotin, folic acid, vitamin $B_{12}$, lipoic acid, ascorbic acid (vitamin C), vitamin A, vitamin D, vitamin E and vitamin K as well as coenzymes thereof.

Minerals include inorganic substances which are required in the human diet and include calcium, iron, zinc, selenium, copper, iodine, magnesium, phosphorus, chromium, and the like and mixtures thereof.

Dietary supplements include, for example, B pollen, bran, wheat germ, kelp, cod liver oil, ginseng, fish oils, amino acids, protein and the like and mixtures thereof.

The preferred nutritional and/or dietary supplements for employment in the present invention include carnitine, calcium, magnesium, ascorbic acid and vitamin E. Carnitine is a naturally occurring amino acid required for mitochondrial oxidation of long-chain fatty acids and is found in all human tissue including skeletal muscle, the liver and the heart. Its role is to transport fatty acids across mitochondrial membranes to be metabolized resulting in the production of ATP (energy). Ingestion of carnitine raises blood levels thereof but does not enhance the clinical-biochemical effects of the naturally occurring carnitine already in the heart when the heart is functioning normally.

During myocardial ischemia, however, carnitine is lost from the ischemic portion of the myocardium. The naturally occurring blood levels of carnitine are not high enough to replenish the carnitine lost in the ischemic portion of the myocardium during an ischemic attack. It has been demonstrated that exogenously administered carnitine, which leads to increased blood levels results in the replenishment of carnitine in the ischemic portion of the myocardium.

Carnitine is a highly water soluble water substance that after absorption is quickly excreted by the kidneys. Therefore there is only a relatively short period in which blood levels of carnitine are sufficient to reenter the ischemic myocardium leading to only temporary protection.

Magnesium, like carnitine, is water soluble and rapidly excreted. A very high percentage of diabetics have magnesium deficiency. This results in a chronic state of increased platelet aggregation and increased sensitivity to angiotensin II. Increased platelet aggregation leads to increased blood clotting and increased angiotension II sensitivity leads to increased vasoconstriction. Both of these effects lead to a decreased blood supply thereby reducing the delivery of natural substances to their intended receptor sites. Multiple daily doses have been required to reverse replenished magnesium stores and normalize the aforementioned abnormalities.

One of the main functions of vitamin E is to enter the lipid layer of arteries to reduce free radical activity thereby reducing the rate of atherosclerosis. Magnesium deficiency will decrease the availability of vitamin E to such receptor sites because of increased blood clotting and vasoconstriction.

In each situation, the present invention provides a substantially continuous supply of nutritional and/or dietary supplements (e.g. carnitine, magnesium, vitamin E and the like) to ensure sufficient blood levels over extended periods of time.

The amount of the active ingredient can be selected in accordance with the current state of the art regarding nutritional and/or dietary substances. The amount of the active ingredient should be chosen to provide the patient with a sufficient amount to meet the requirements of the consumer if the composition is delivered as little as once over a 24 hour period. By way of example, carnitine is provided in an amount from about 0.075 to 20 grams, preferably 0.5 to 6 grams. Calcium is provided in an amount of from about 0.01 to 3.0 grams, preferably 0.5 to 2.0 grams. Magnesium may be present in the composition of the invention in an amount of from about 0.1 to 3.0 grams, preferably 0.2 to 1.0 gram. Ascorbic acid is generally present in an amount of from about 0.01 to 3.0 grams, preferably 0.075 to 1.0 gram. Vitamin E may be present in an amount of from about 10 to 3000 IU, preferably 30 to 1000 IU.

The active ingredients in accordance with the present invention are in the free form of the compound and in a substantially sustained-release form (i.e. microencapsulated). By way of example, the free form compounds may be water soluble while the sustained-release compounds may be water insoluble.

Microencapsulation of the active ingredient is a process in which the active ingredient is coated with a continuous film of a natural or synthetic polymer. Methods of microencapsulation are known such as described in A. Lieberman Pharmaceutical DOSAGE FORMS: TABLETS—Volume I, Second Edition, New York (1989) pp. 372–376. One such method is by the addition of a non-solvent of the polymer and then hardening of the membrane so that the microcapsule can be separated from the vehicle by filtration or centrifuging or the like. The rate of delivery of the encapsulated active ingredient can be controlled as a function of the type of polymer used to encapsulate the active ingredients, the thickness of the polymer layer or both.

Another method of microencapsulating an active ingredient includes processing three mutually immiscible phases, one containing the active ingredient, one containing the microencapsulating coating material (e.g. ethyl cellulose) and one containing a liquid vehicle used only in the manufacturing phase. The three phases are mixed and the coating material is thereby absorbed on the active ingredient. The next step involves converting the coating material to a substantially solid form by cross-linking or the like.

Microencapsulation of a water insoluble substance can also function to mask unpleasant tastes but is principally used in the present invention for slowing down the rate of release of the active ingredient to provide a sustained-release formulation.

The microencapsulated active ingredient will generally comprise from about 3% to 50% by weight of the encapsulating polymer and from about 50% to 97% of the active ingredient. The polymer constituting the encapsulating membrane must be permeable or soluble in the gastrointestinal juices in order to allow the release of the active ingredient and its absorption.

The polymers which may be employed in the present invention for microencapsulating the active ingredient include polyacrylates, polymethacrylates, polyvinylchloride, polyvinylalcohol, polyethylene, polyamides, polysiloxanes, cellulose derivatives including ethylcellulose and the like. Ethylcellulose is the preferred polymer for microencapsulation.

The effervescent agent employed in the present composition serves to evolve gas by means of a chemical reaction which takes place upon exposure of the effervescent agent to the saliva in the mouth or to water or other suitable liquid. The gas generating reaction is typically the result of the reaction of a soluble acid source and an alkali metal or alkaline earth metal carbonate or carbonate source. The reaction of these two compounds produces carbon dioxide gas upon contact with water.

The acid sources generally include food acids, acid anhydrides and acid salts. Food acids include citric acid, tartaric acid, malic acid, fumaric acid, adipic acid, and succinic acids, combinations thereof and the like. Acid anhydrides of the above acids may also be used. The acid salts typically are selected from sodium, dihydrogen phosphate, disodium dihydrogen pyrophosphate, acid citrate salts and sodium acid sulfite.

The carbonate sources include dry solid carbonate and bicarbonate salts such as sodium bicarbonate, sodium carbonate, potassium bicarbonate, potassium carbonate, magnesium carbonate, sodium sesequicarbonate, sodium glycine carbonate, L-lysine carbonate, arginine carbonate and amorphous calcium carbonate.

The amount of the acid component and the bicarbonate component can vary over a wide range. Generally, equal amounts of the two components of the effervescent agent are preferred.

The amount of the effervescent agent in the composition of the present invention can also vary over a wide range. For the formation of tablets, the effervescent agent will typically comprise from about 5 to 50% by weight of the final composition. The amount of the effervescent agent should be sufficient to produce a rapid and complete disintegration of the formulation when placed in water. Disintegration should occur in water without stirring or other mechanical means for dissolution.

The present composition may include one or more additives chosen typically from flavors, colors, binders, fillers, disintegrants and the like. Examples of binders include acacia, tragacanth, gelatin, starch and the like.

Disintegrants include starches, bentonite, gums, alginates and the like.

Coloring agents are those suitable for food and include both natural and synthetic coloring agents.

Flavors which may be incorporated into the present composition are selected from natural and synthetic oils and flavor aromatics or combination thereof including extracts from plants, leaves, flowers, fruits and the like. Typical flavoring agents include cinnamon oil, oil of wintergreen, peppermint oils, clove oil and the like.

The amount of the individual additives may vary over and under range. Binders can be present in amounts up to 60% by weight of the composition. Coloring agents are typically present in an amount of no more than up to 3.5% by weight of the total composition.

In typical cases, the total amount of the additives does not exceed about 25% by weight of the composition.

The nutritional and/or dietary composition of the present invention can generally be prepared by first preparing the effervescent agent (e.g. sodium bicarbonate and citric acid) in dry form.

A microencapsulated form of the active ingredient (e.g. magnesium chloride, vitamin E, carnitine) is combined with the free form amount of each ingredient. A mixture of the effervescent agent and the active ingredients in both microencapsulated and free form are combined and formed into suitable tablets.

Tablets incorporating the composition of the present invention can be prepared by well known tabletting methods. For example, the composition is deposited into a cavity and then a compressive force is applied by a punching device. The tabletted material is thus formed into the shape formed by the punching device and the cavity.

EXAMPLE 1

A quantity of sodium bicarbonate sufficient to provide one gram per tablet is passed through a one mm screen and then loaded into a fluid bed. Deionized and sterile water (filtered through a ligacon membrane) into the fluid bed immediately with the commencement of the injection of dry air through the inlet of the fluid bed. The dry air inlet is accompanied with the nebulization of at least 5.5 liters of water at a pressure of around 8 atm for about 10 to 12 minutes. Then the sodium bicarbonate is dried with dry air at a temperature of 33° to 40° C. to form a granulate.

When the internal temperature of the granulate reaches room temperature the influx air is stopped and citric acid (1.3 g per tablet) is added directly into the fluid bed. The mixture is homogenized and sterile water is nebulized into the vessel while under mixing. The granulate is dried in dry air (50° C.) until a final temperature of the granule (45° to 50° C.) is reached. The warming up of the dry air is stopped, but the incoming stream of air is continued until the granule is at a temperature of 30° C.

Vitamin C, Vitamin E and magnesium oxide are micro encapsulated in the following manner:

0.4 g of ascorbic acid, 400 I.U of vitamin E and 0.5 g of magnesium oxide are granulated in a vessel. A solution of cellulose acetophthalate is added to the vessel under stirring to form a granulate of the respective active ingredients.

The granulate is dispersed in demineralized water under stirring so that cellulose acetophthalate precipitates on the agglomerated particles with the salification of the solution. Subsequently an acid solution is injected to complete the coating operation and to initiate hardening of the microencapsulation coating. The product is filtered, dried in a fluid bed and passed through a screen to select microcapsules of the desired size. The microcapsules are combined with suitable amounts of the free form of each of the active ingredients (i.e. amounts similar to those used for forming microcapsules). The dry mixture of both the free and microencapsulated forms of the active ingredients is pressed into tablets in a humidity controlled area at a temperature of about 20° C. The resulting tablets contain the active ingredients in both free form and microencapsulated form in the presence of the effervescent agent.

EXAMPLE 2

The process of Example 1 is repeated except that the active ingredients used to form the microcapsules are added to an organic medium such as cyclohexane. A solution of ethyl cellulose is added to the vessel under stirring to form a granulate of the respective active ingredients. The granulate is then cooled to harden the coating of the microcapsules. The product is then filtered, dried in a fluid bed and passed through a screen to select microcapsules of the desired size.

EXAMPLE 3

The process of Example 1 is repeated except that the active ingredients include carnitine tartrate and ascorbic acid wherein the amounts of each of the active ingredients for both the free and microencapsulated form components are 3.0 g and 0.5 g per tablet.

What is claimed is:

1. A composition comprising:
   (a) at least one active ingredient including carnitine in amounts sufficient to provide a dosage form of said active ingredient as few as once in a 24 hour period, said active ingredients being in both a free form component and a microencapsulated component which has sustained-release properties; and
   (b) an effective amount of an effervescent agent.

2. A composition comprising:
   (a) at least one active ingredient including anyone of calcium, magnesium, ascorbic acid, vitamin E and combinations thereof in amounts sufficient to provide a dosage form of said active ingredient as few as once in a 24 hour period, said active ingredients being in both a free form component and a microencapsulated component which has sustained-release properties; and
   (b) an effective amount of an effervescent agent.

3. A method of providing to a warm-blooded animal a nutritional or dietary supplement or combination thereof, comprising administering to said warm-blooded animal the composition of claim 2.

4. The composition of claim 1 wherein the active agent is selected from the group consisting of carnitine, calcium, magnesium, ascorbic acid, vitamin E and combinations thereof.

5. The composition of claim 1 in the form of a tablet or granules dissolvable in water.

6. The composition of claim 1 wherein the microencapsulated component comprises said active ingredient contained within a polymer coating.

7. The composition of claim 6 wherein the polymer coating is made of ethylcellulose.

8. The composition of claim 1 wherein carnitine is present in an amount of from about 0.75 to 20 grams.

9. The composition of claim 4 wherein calcium is present in an amount of 0.01 to 3.0 grams.

10. The composition of claim 4 wherein magnesium is present in an amount of from about 0.1 to 3.0 grams.

11. The composition of claim 4 wherein ascorbic acid is present in an amount of from about 0.01 to 3.0 grams.

12. The composition of claim 1 wherein vitamin E is present in an amount of from about 10 to 3000 IU.

13. The composition of claim 1 wherein the effervescent agent is the combination of an acid and an alkali metal or alkaline earth metal carbonate.

14. The composition of claim 1 wherein the active ingredients are selected from water soluble compounds, water insoluble compounds and combinations thereof.

15. The composition of claim 14 wherein the free form component is water soluble.

16. The composition of claim 14 wherein the sustained-release component is water insoluble.

17. A method of providing to a warm-blooded animal a nutritional or dietary supplement or combination thereof, comprising administering to said warm-blooded animal the composition of claim 1.

18. The composition of claim 2 wherein the sustained-release component is water insoluble.

19. The composition of claim 2 wherein the active agent further includes carnitine.

20. The composition of claim 2 in the form of a tablet or granules dissolvable in water.

21. The composition of claim 2 wherein the microencapsulated component comprises said active ingredient contained within a polymer coating.

22. The composition of claim 21 wherein the polymer coating is made of ethylcellulose.

23. The composition of claim 2 wherein calcium is present in an amount of 0.01 to 3.0 grams.

24. The composition of claim 2 wherein magnesium is present in an amount of from about 0.1 to 3.0 grams.

25. The composition of claim 2 wherein ascorbic acid is present in an amount of from about 0.01 to 3.0 grams.

26. The composition of claim 2 wherein vitamin E is present in an amount of from about 10 to 3000 IU.

27. The composition of claim 2 wherein the effervescent agent is the combination of an acid and an alkali metal or alkaline earth metal carbonate.

28. The composition of claim 2 wherein the free form component is water soluble.

* * * * *